United States Patent [19]

Kitsuki et al.

[11] Patent Number: 5,136,112
[45] Date of Patent: Aug. 4, 1992

[54] PROCESS FOR PREPARING 2-HYDROXY-2 5, 5, 9-TETRAMETHYLDECALYL ETHANOL

[75] Inventors: Tomohito Kitsuki, Wakayama; Yoshiaki Fujikura, Utsunomiya, both of Japan

[73] Assignee: Kao Corporation, Tokyo, Japan

[21] Appl. No.: 736,927

[22] Filed: Jul. 29, 1991

[30] Foreign Application Priority Data

Aug. 15, 1990 [JP] Japan ................... 2-215294

[51] Int. Cl.$^5$ .................. C07O 35/27; C07O 35/23
[52] U.S. Cl. .................. 568/819; 568/816; 568/817
[58] Field of Search ............ 568/819, 816, 817

[56] References Cited

U.S. PATENT DOCUMENTS 4,633,011 12/1986 Büchi et al. .................. 568/819

OTHER PUBLICATIONS

Sousa et al., "J. Organic Chem." vol. 25 pp. 108 110 (Jan. 1960).

Primary Examiner—Werren B. Lone
Attorney, Agent, or Firm—Oblon, Spivak, McClelland, Maier & Neustadt

[57] ABSTRACT

A process for preparing 2-hydroxy-2, 5, 5, 9-tetramethyldecalyl ethanol of formula (II):

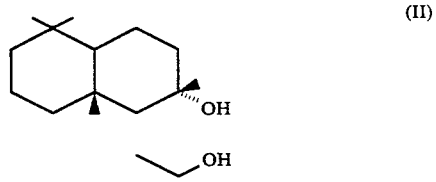

which comprises reducing 3a, 6, 6, 9a-tetramethyldecahydro-naphto[2, 1-b]furan-2(1H)-one of formula (I):

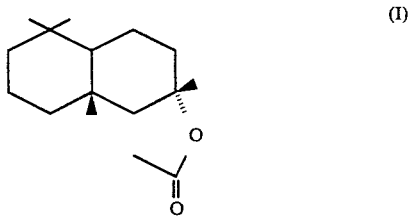

with an alkali metal boron hydride in the presence of a hydroxyl ether compound.

4 Claims, No Drawings

PROCESS FOR PREPARING 2-HYDROXY-2 5, 5, 9-TETRAMETHYLDECALYL ETHANOL

BACKGROUND OF THE INVENTION i) Field of the Invention

This invention relates to a novel process for preparing 2-hydroxy-2, 5, 9-tetramethyldecalyl ethanol which is useful as an intermediate in the synthesis of a fragrance.

ii) Description of the Background Art 3a, 6, 6, 9a-Tetramethyl-(3ar, 5at, 9ac, 9bt)-dodecahydro-naphto2 1-b]furan (hereinafter referred to as ambrox) is an odorlferous substance which characterizes the odor of ambergris, and it is indispensable for compounding amber-note fragrances. Conventionally, the following synthesis route via norambrenolide (I) as a synthesis intermediate has been taken as most advantageous, where the starting material is either sclareol obtained from vegetable essential oil or α-(orα-) monocyclohomofarnesic acid derived from dihydro α-(orα-)ionone:

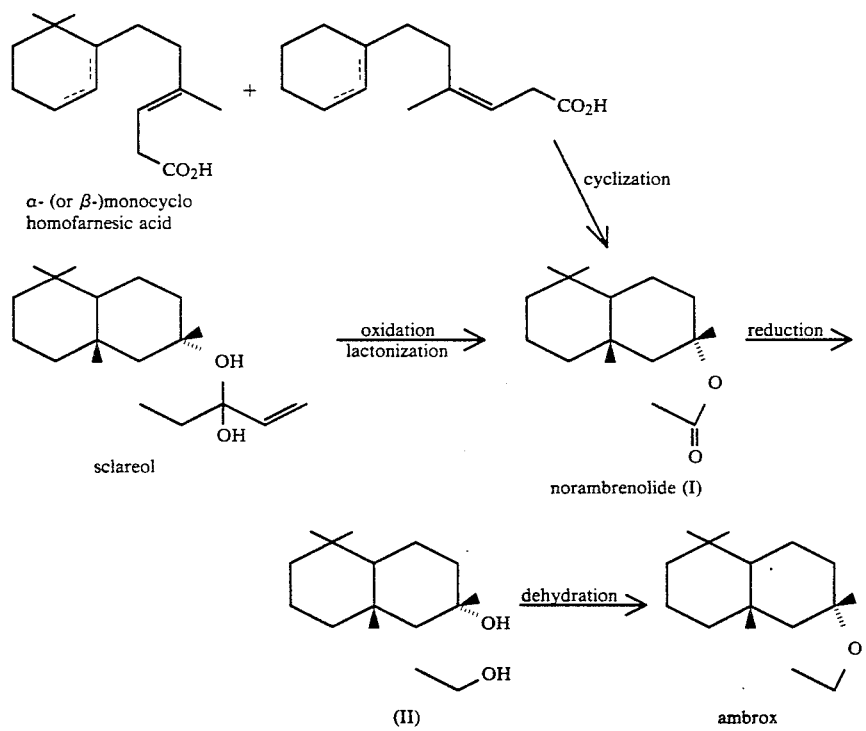

α- (or β-)monocyclo homofarnesic acid sclareol norambrenolide (I)

(II)

ambrox

Reports have been published for the various reaction steps. Among the processes for obtaining compound (II), which is 2-hydroxy-2, 5, 5, 9-tetramethyldecalyl ethanol (hereinafter referred to as diol), by reducing compound (I). which is 3a, 6, 6, 9a-tetramethyl-decahydro-naphto[2, 1-b]furan-2(1H)-one (hereinafter referred to as norambrenolide), the following processes are known to give a high yield:

1) A process which uses lithium aluminum hydride.
2) A process which uses bis-(2-methoxyethoxy)-sodium aluminum hydride (Japanese Patent Application (Kokai) No. 239481/1985).

The process 1), however, is neither convenient nor economical because lithium aluminum hydride is expensive, and special care must be taken since the compound is very sensitive to moisture. Additionally, solvents to be used must be purified under strict control. The process 2), on the other hand, uses a significant amount of an expensive reagent, namely, 50-200% by weight of bis-(2-methoxycthoxy)-sodium aluminum hydride based on the total amount of a starting material. Thus this process is not economical.

In the meantime, a process utilizing a mixed solvent of t-butanol and methanol has recently been proposed for reducing lactones with sodium boron hydride [*Bull. Chem. Soc. Jpn.*, 57, 1948-1953(1984)]. Although this process has been attempted for the reduction of norambrenolide, it was found that the process requires sodium boron hydride in an amount of more than 31% by weight, based on the substrate; and a significant amount of solvent, i.e.. more than ten times (1000%) by volume (or seven times (700%) by weight) of the substrate for completing the reaction. Therefore, from the viewpoint of productivity and economy, this process is not suitable for production on an industrial scale.

Accordingly, it has been hoped to develop a new process for reducing norambrenolide with a reagent which is easy to-obtain and inexpensive so as to obtain diol (II) at a high yield.

SUMMERY OF THE INVENTION

Under the above-mentioned circumstances, the present inventors have made extensive studies and have found that the diol (II) can be produced efficiently, on an industrial scale, by reducing norambrenolide with an alkali metal boron hydride in the presence of a compound having, in the molecule thereof a hydroxyl group and an ether bond. The present invention was accomplished based upon this finding.

An object of this invention, therefore, is to provide a process for preparing diol (II).

The process of the present invention is expressed by the following reaction scheme wherein M is an alkali metal atom:

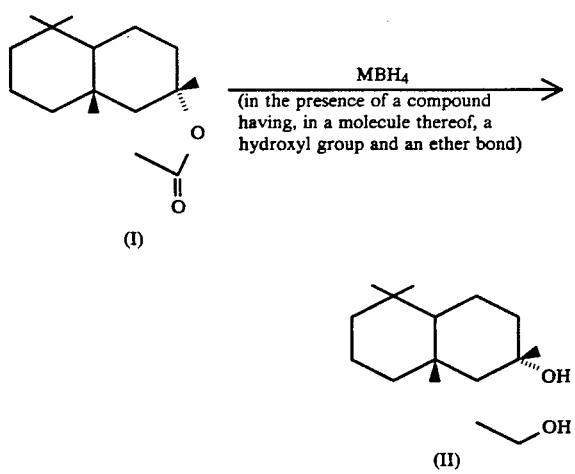

Namely, the present invention provides a process for preparing diol (II) which comprises a step of reducing norambrenolide with an alkali metal boron hydride in the presence of a compound having in the molecule thereof a hydroxyl group and an ether bond.

DETAILED DESCRIPTION OF THE INVENTION AND PREFERRED EMBODIMENTS

In the present invention, compounds expressed by the following formula (III) are used as the compound having. in the molecule thereof, a hydroxyl group and an ether bond (hereinafter referred to as hydroxyl ether compound):

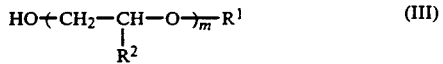

wherein $R^1$ is a $C_1$-$C_{12}$ alkyl or alkenyl group, $R^2$ is a hydrogen atom or a $C_1$-$C_6$ alkyl group, m is a number of 1 to 20, and when m=1, $R^1$ and $R^2$ may together form a $C_3$-$C_5$ alkylene group.

Examples of the above compounds include ethylene glycol monoalkyl ethers, diethylene glycol monoalkyl ethers, triethylene glycol monoalkyl ethers, cyclic ether alcohols, with preferred compounds including etbylene glycol monoethyl ether, ethylene glycol monobutyl ether diethylene glycol monoethyl ether diethylene glycol monobutyl ether, triethylene glycol monoethyl ether triethylenc glycol monobutyl ether and tetrahydro furfuryl alcohol.

Examples of alkai metal boron hydrides include sodium boron hydride, potassium boron hydride and lithium boron hydride.

In the present invention it is preferred that the amount of the alkali metal boron hydride be about 15 to 31% by weight of the amount of the norambrenolide and the amount of the hydroxyl ether compound be about 100 to 214% by weight of the amount of the norambrenolide. Although the process according to this invention can be carried out without using a solvent, it is preferred to use a solvent for making efficient use of the alkali metal boron hydride and the hydroxyl ether compound. Any amount of solvent may be used so far as it is sufficient for dissolving the norambrenolide. However, it is preferable, from the viewpoint of the productivity on an industrial scale and of the economy, that the amount of the solvent be about 100 to 400% by weight of the amount of the norambrenolide.

Examples of the reaction solvent include aliphatic hydrocarbons such as n-hexane n-heptane, n-octane: aromatic hydrocarbons such as benzene, toluene, xylene: and ethers such as diethylether, tetrahydrofuran dioxane, dimethyl cellosolve and diglyme.

The reaction is carried out by slowly dropping the hydroxyl ether compound into a mixture of the norambrenolide, the alkali metal boron hydride and the solvent. Although any temperature between 0° to 150° C. is suitablc for the reaction, the range of 50° to 150° C. is, on a practical basis, the best because the reaction speed increases as the reaction temperature rises.

Since the diol (II) is produced at a high yield in the reaction mixture, the resultant mixture may be used, as is, as a starting material for the production of the ambrox. Alternatively, the diol (II) may be isolated and purified by a conventional purifying method such as rinsing and recrystallization.

In the present invention norambrenolide is quantitatively reduced in a short time with a hydroxyl ether compound without the use of a significantly excessive amount of an alkali metal boron hydride. As a result, diol (II) can be manufactured efficiently on an industrial scale.

Having now generally described this invention, a further understanding can be obtained by reference to certain specific example which is provided herein for purposes of illustration only and is not intended to be limiting unless otherwise specified.

EXAMPLE

Into a mixture containing 2.5 g (0.066 mol) of sodium boron hydride, 8.0 g (0.032 mol) of norambrenolide and 20 g of xylene. 17.1 g (0.127 mol) of diethylene glycol monoethyl ether was dropped at 90° C. over 2 hours while stirring. Subsequently, stirring was continued for 1 hour at the same temperature. Then, 8 g of glycerine and 40 g of water were added thereto at 70° C. stirred at the same temperature for 1 hour, and allowed to stand, followed by separation of the lower layer. The xylene layer containing the produced diol (II) was washed twice with saturated NaCl solution. The solvent was distilled off under reduced pressure and the residue was recrystallized from n-hexane to obtain 7.7 g of diol (II) as white crystals (yield : 95.3%).

The diol (II) was converted to an ambrox by dehydration according to a known method (Japanese Patent Application Laid-open (Kokai) No. 33184/1986). The obtained ambrox was confirmed to be identical with a standard sample Ambroxan (product of HENKEL Inc.) by GLC (Silicone OV-17(2%), 5×2.6 φ,1 m).

COMPARATIVE EXAMPLE

Into a mixture containing 1.25 g (0.033 mol) of sodium boron hydride, 4.0 g (0.016 mol) of norambrenolide and 40 ml of t-butanol. 8 ml of methanol was dropped over 1 hour while stirring and refluxing. Thereafter stirring was continued for 5 hours at the same temperature. Water was added thereto at 60° C. and extraction was conducted 3 times with ether. An organic layer was condensed under reduced pressure and the residue was treated by silica gel column chromatography (solvent; n-hexane : ether=1 : 1) to obtain 3.26 g of diol (II) (yield : 80.3%) and 0.72 g of unreacted norambrenolide.

What is claimed is:

1. A process for preparing 2-hydroxy-2, 5, 5, 9-tetramethyldecalyl ethanol of formula (II):

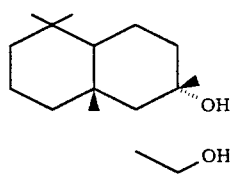

which comprises reducing 3a, 6, 6, 9a-tetramethyl-decahydro-naphto [2,1-b]furan-2](1H)-one of formula (I):

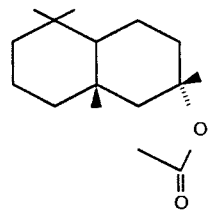

with an alkali metal boron hydrode in the presence of a compound having, in the molecule thereof, a hydroxyl group and an ether bond, wherein said compound having said hydroxyl group and ether bond is a compound of formula (III).:

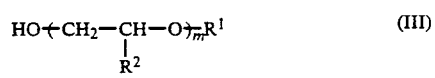

wherein $R^1$ is a $C_1$-$C_{12}$ alkyl or alkenyl group, $R^2$ is a hydrogen atom or a $C_1$-$C_6$ alkyl group, m is a number of 1 to 20, and when m=1, $R^1$ and $R^2$ may together form a $C_3$-$C_5$ alkylene group, under temperature conditions such that reduction is effected.

2. The process as defined in claim 1, wherein the amount of said alkali metal boron hydride is about 15 to 31% by weight of the amount of compound (I).

3. The process as defined in claim 1, wherein the amount of said compound having, in the molecule thereof, a hydroxyl group and an ether bond is about 100 to 214% by weight of the amount of compound (I).

4. The process as defined in claim 1, wherein said process is carried out in the presence of a solvent in an amount of about 100 to 400% by weight of the amount of compound (I).

* * * * *

UNITED STATES PATENT AND TRADEMARK OFFICE
CERTIFICATE OF CORRECTION

PATENT NO. : 5,136,112
DATED : August 4, 1992
INVENTOR(S) : Tomohito Kitsuki et al It is certified that error appears in the above-indentified patent and that said Letters Patent is hereby corrected as shown below:

On the title page at Section 57, Formula II should appear as:

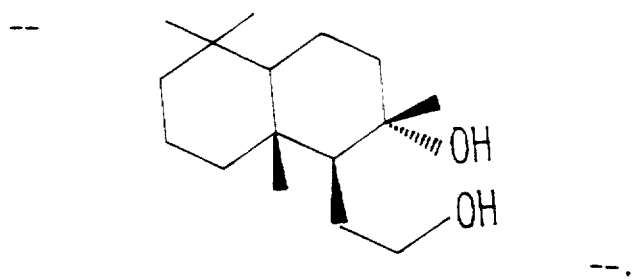

--.

On the title page at section 57, Formula I should appear as:

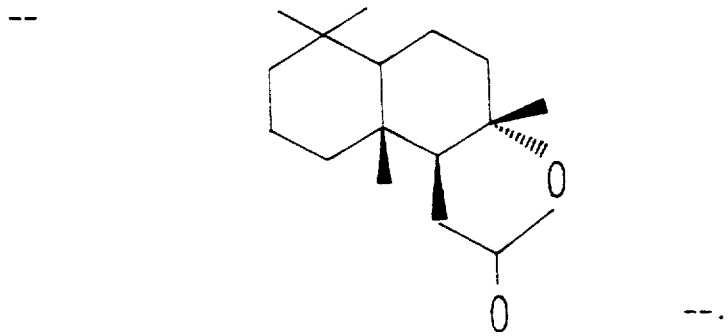

--.

UNITED STATES PATENT AND TRADEMARK OFFICE
CERTIFICATE OF CORRECTION

PATENT NO. : 5,136,112
DATED : August 4, 1992
INVENTOR(S) : Tomohito Kitsuki et al It is certified that error appears in the above-indentified patent and that said Letters Patent is hereby corrected as shown below:

The formulas of the second and third lines in columns 1 and 2 should appear as:

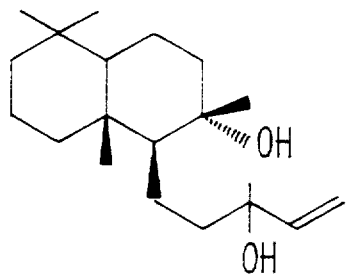

sciareol oxidation
iactonization

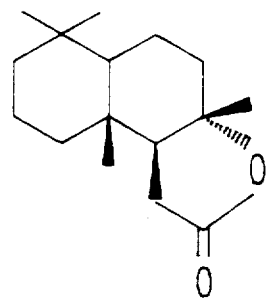

norambrenolide (I)

reduction

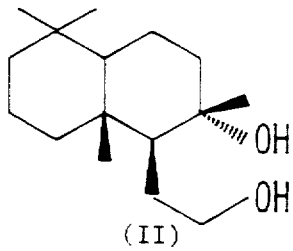

(II)

dehydration

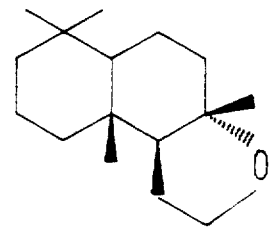

ambrox

UNITED STATES PATENT AND TRADEMARK OFFICE
CERTIFICATE OF CORRECTION

PATENT NO. : 5,136,112
DATED : August 4, 1992
INVENTOR(S) : Tomohito Kitsuki et al It is certified that error appears in the above-indentified patent and that said Letters Patent is hereby corrected as shown below:

The formula of lines 5-10 of column 3 should be as follows:

--

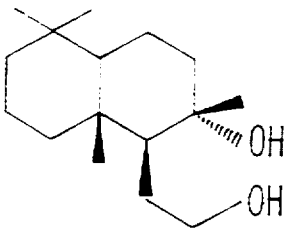

(II)

--.

The formula of lines 15-20 of column 3 should be as follows:

--

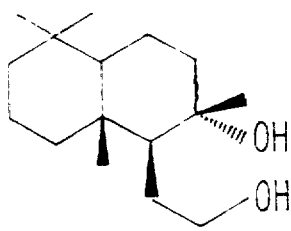

(II)

--.

UNITED STATES PATENT AND TRADEMARK OFFICE
CERTIFICATE OF CORRECTION

PATENT NO. : 5,136,112
DATED : August 4, 1992
INVENTOR(S) : Tomohito Kitsuki et al It is certified that error appears in the above-indentified patent and that said Letters Patent is hereby corrected as shown below:

Column 5, line 25, Formula II should appear as:

-- 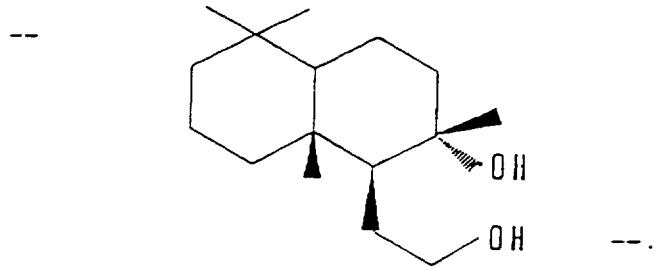 --.

UNITED STATES PATENT AND TRADEMARK OFFICE
CERTIFICATE OF CORRECTION

PATENT NO. : 5,136,112
DATED     : August 4, 1992
INVENTOR(S) : Tomohito Kitsuki et al It is certified that error appears in the above-indentified patent and that said Letters Patent is hereby corrected as shown below:

Column 6, line 5, Formula I should appear as:

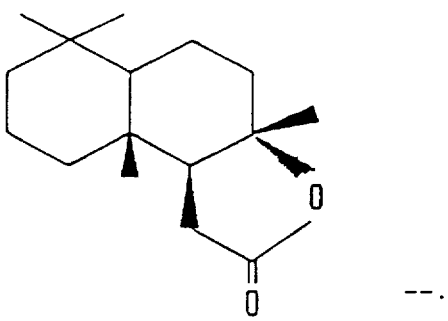

Column 6, line 12, "hydrode", should read --hydride--.

Signed and Sealed this

Fourteenth Day of December, 1993

Attest:

BRUCE LEHMAN

Attesting Officer    Commissioner of Patents and Trademarks